United States Patent [19]

Roger

[11] Patent Number: 4,846,161
[45] Date of Patent: Jul. 11, 1989

[54] METHOD AND APPARATUS FOR REMOVING PROSTHETIC CEMENT

[76] Inventor: Gregory J. Roger, 5 Kent Street, Collaroy, Australia, 2098

[21] Appl. No.: 90,797
[22] PCT Filed: Oct. 28, 1986
[86] PCT No.: PCT/AU86/00321
§ 371 Date: Aug. 20, 1987
§ 102(e) Date: Aug. 20, 1987
[87] PCT Pub. No.: WO87/02571
PCT Pub. Date: May 7, 1987

[30] Foreign Application Priority Data

Oct. 28, 1985 [AU] Australia .............................. PH3128
Jun. 5, 1986 [AU] Australia .............................. PH6275

[51] Int. Cl.[4] ............................................ A61B 17/32
[52] U.S. Cl. ............................... 128/92 V; 128/92 VP; 128/317
[58] Field of Search ......... 128/92 VM, 92 VK, 92 V, 128/92 VP, 317; 623/22, 92 R, 92 VQ, 92 VJ, 92 VL; 30/166 R

[56] References Cited

U.S. PATENT DOCUMENTS

| 2,339,843 | 1/1944 | Dillon | 30/166 R |
| 2,966,931 | 1/1961 | Dreier | 30/166 R |
| 4,248,232 | 2/1981 | Engelbrecht et al. | 128/92 V X |
| 4,399,813 | 8/1983 | Barber | 128/92 VT |
| 4,612,922 | 9/1986 | Barber | 128/92 R X |
| 4,617,930 | 10/1986 | Saunders | 30/166 R |
| 4,696,292 | 9/1987 | Heiple | 128/92 V |
| 4,702,236 | 10/1987 | Tarabichy et al. | 128/92 V |

Primary Examiner—Robert A. Hafer
Assistant Examiner—Kevin G. Rooney
Attorney, Agent, or Firm—Fleit, Jacobson, Cohn, Price, Holman & Stern

[57] ABSTRACT

A device, and method of producing and using same, for use in removing the prosthetic cement from a bone in which an artificial joint (such as hip joint) is to be replaced. The device cuts the prosthetic cement in a longitudinal plane of the prosthetic cavity to the complete depth or the cement but without substantially cutting into the bone. The device includes a reciprocating saw head (8) which is advanced longitudinally of the cavity and maintained within the preselected longitudinal plane of the cavity by a guide (1) while it cuts through the cement (10). The saw head (8) is transversly biased towards the cement so that it cuts only to a depth defined by the profile of a template (6). The profile of the template (6) is obtained from X-ray information obtained before commencement of the operation.

13 Claims, 4 Drawing Sheets

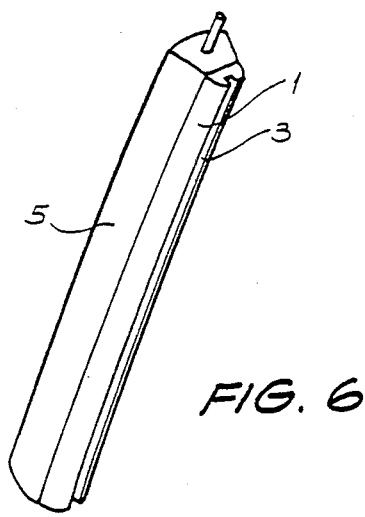
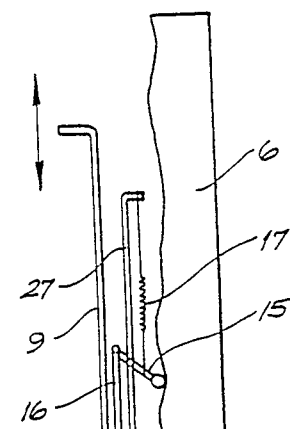
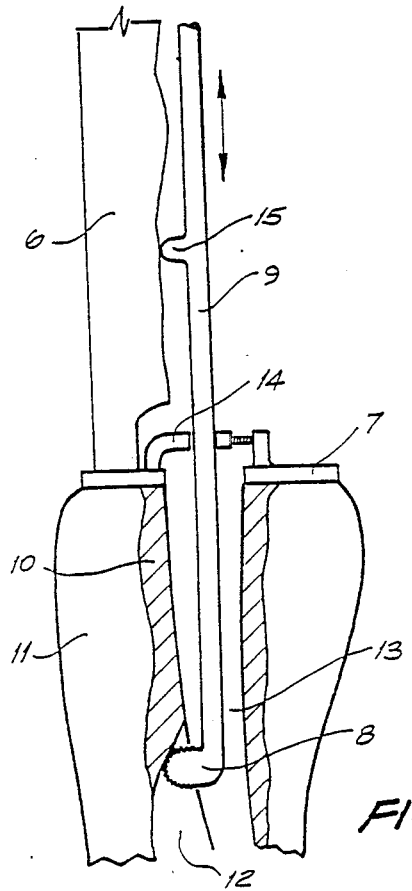
FIG. 6
FIG. 7
FIG. 8

METHOD AND APPARATUS FOR REMOVING PROSTHETIC CEMENT

BACKGROUND ART

The present invention relates to a method and apparatus for the removal of prosthetic cement from the bone of a patient undergoing total joint replacement, particularly total hip joint replacement.

Some prostheses, used in total hip replacements especially those used in early procedures, included long stems which were embedded in prosthetic cement within a suitable cavity within the bone. Loosening of such prostheses requires that they be removed and replaced. Many such prostheses last approximately five to ten years before loosening. The major problem in the removal and replacement of the original prosthesis is found in the removal of the prosthetic cement which is normally polymethylmethacrylate.

The removal of the cement is usually effected with hammer and chisel. The surgeon is working within a live bone, down a narrow curved cylindrical cavity with poor lighting and visibility. Also used, on some occasions, are tungsten burr drills, assorted reeming drills, more recently experimental laser cutting devices, and alternative surgical techniques which involve making a "window" in the bone in a position corresponding to where it is thought the prosthetic cement finishes and then removing the cement from below.

These techniques are poor in that they are of long duration and generally place the live bone in risk of damage. Damage, such as facture, can be a serious problem because many of the patients are elderly.

DISCLOSURE OF THE INVENTION

In one broad form the present invention may be said to provide a template profiled so as to correspond to the profile of the line of intersection of a generally longitudinal pre-selected plane of a joint prosthesic cavity and the associated prosthetic cement/bone interface of a patient.

An alternative broad form of the invention can be said to provide a method of forming a guide means for use in removing prosthetic cement from a bone of a patient comprising the steps of determining the profile of the prosthetic cement/bone interface along a predetermined line running longitudinally of the bone and forming said guide means adapted to guide a suitable cutting means such that it cuts through the cement along said lines substantially without cutting into the bone.

Broadly speaking the invention can also be said to provide a method of producing a template, such as the template described above, including the steps of:
  scanning the patient in the area of the joint prosthesis so as to obtain a profile of the prosthetic cement/bone interface at its intersection with the longitudinal pre-selected plane of the cavity; and
  feeding the profile into a machine which, in response thereto, forms the template being profiled correspondingly to the profile of the line of intersection of the pre-selected plane and the cement/bone interface.

Preferred apparatus of the invention can be said to comprise:
  the template as described above;
  a linear saw guide being rigidly attached to, or integral with, the template;
  a saw adapted for reciprocating cutting action and traversable along the guide for linear advancement of the cutting action; and
  a template follower urging the saw to cut along a path being substantially the line of intersection of the pre-selected plane and the cement/bone interface.

In a particular preferred embodiment the template may be the base of a groove of a saw guide.

In another particular preferred embodiment the template may be the saw which is advanced transversely of the guide, in which case no template follower is required.

Another broad form of the invention may be said to provide a method of longitudinally cutting prosthetic cement in a bone of a patient, using the above-described apparatus, and comprising:
  positioning the guide and template fixedly relative to the prosthetic cavity approximately in the longitudinal pre-selected plane associated with the template profile;
  introducing the saw cooperatively to the guide;
  commencing reciprocating cutting action of the saw, and
  advancing the saw such that a groove is cut into the prosthetic cement to a depth approximately equal to the depth of the cement and substantially without cutting into the bone.

In a preferred method of the invention a number, usually 3 or 4, of longitudinal cuts are produced in the prosthetic cement spaced apart about the cavity and produced by the above method.

BRIEF DESCRIPTION OF THE DRAWINGS

FIG. 6 schematically shows an alternative device embodying the invention;

FIG. 7 schematically shows a further device embodying the invention, the device being shown in place within a bone;

FIG. 8 is similar to FIG. 7 but shows an alternative device embodying the invention;

BEST MODE OF CARRYING OUT THE INVENTION

Figure 1:
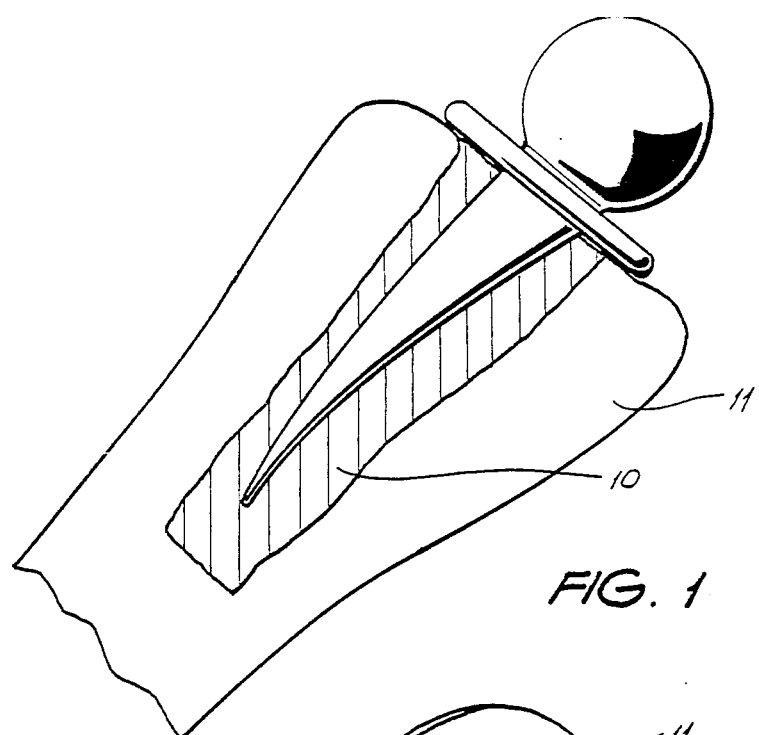
FIG. 1 schematically shows an artificial joint prosthesis fixed in a bone.
Figure 2:
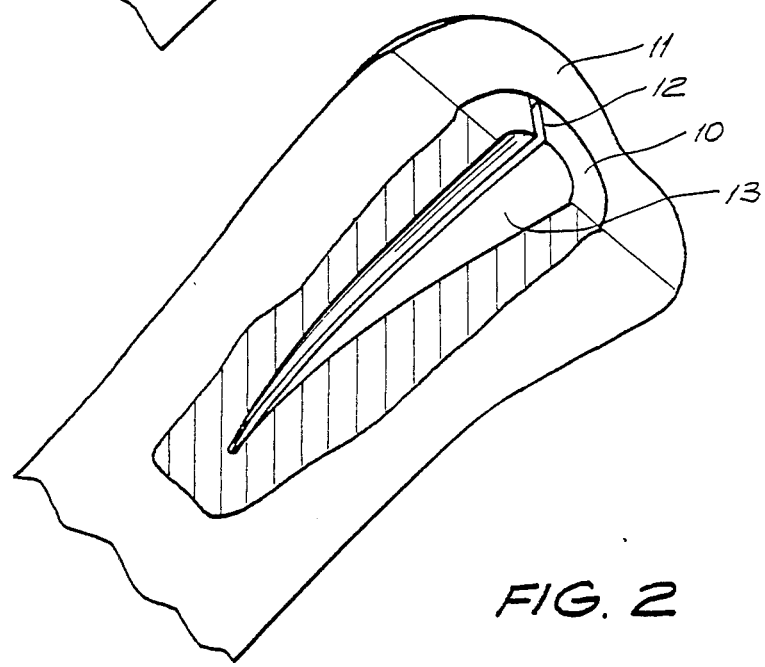
FIG. 2 schematically shows in longitudinal cross-section a bone in which the prosthetic cement has been cut.

As seen in FIG. 1 the femoral prosthesis stem is held in place in the femur of a patient by a cement, which is normally polymethylmethacrylate (PMMA). If the prosthesis has to be removed for any reason it can normally be pulled relatively easily from the cement leaving a closed end tubular cement plug within the bone which must then be removed to allow a fresh prosthesis to be inserted and re-cemented.

In the process of removing the prosthetic cement, the present invention allows it to be cut to the depth of the cement in a longitudinal line without cutting into the bone by any substantial amount. Normally 3 or 4 of such cuts are made so as to be spaced apart around the perimeter of the plug.

It is well known to use X-ray machines linked with computer analysis equipment in order to produce three-dimensional representations of hidden bones etc. Such machinery and associated skills can be adapted to control the cutting machine. The cutting machine produces a template which has a face or edge which is shaped so as to correspond to the contour of the line of intersection of the prosthetic cement and the bone at a preselected generally longitudinally running plane of the joint prosthesic cavity. The correspondence of the template profile to that of the actual cement/bone interface will depend upon such aspects as the device which will be used to follow the template profile, the geometry of the guiding means and saw during advancement of the saw and the cutting head intended for use in carrying out the operation. There might, for example, be a scaling factor between the actual bone/cement interface shape and the shape of the template.

In broad terms the cutting operation is carried out by guiding a reciprocating saw blade within the prosthetic cement cavity, the final depth of cut along the cutting controlled by the profile of a template so as to cut entirely through the cement without substantially cutting the bone.

Frequently a bottom plug of the prosthetic cement is simply bored out using conventional equipment. The axis of this boring should be aligned with the cuts which are to be made so that the cuts can continue into the bored out section.

Particular embodiments of the invention will now be discussed in detail.

Figure 3:
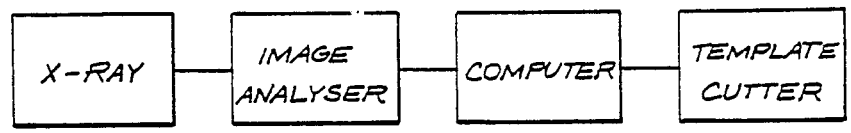
FIG. 3 schematically shows equipment used in producing devices of the invention.
Figure 4:
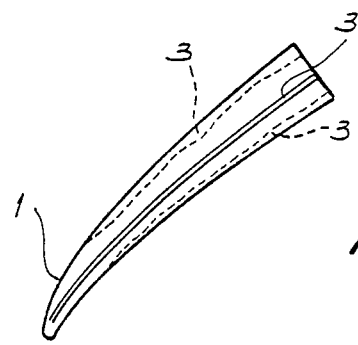
FIGS. 4 and 5 schematically show two slightly differing embodiments of the invention.

A guide blank 1 is shaped substantially the same as the stem of the prosthesis which is to be removed as shown in FIG. 4. The guide blank 1 is machined by the cutting device 2 under the control of the equipment shown in FIG. 3 and as generally described above. The cutting machine 2 produces a groove 3 within the guide 1, the depth of the groove 3 varying along its length so as to be of substantially the same profile as the cement/bone interface at the intersection of the corresponding preselected plane. The groove 3 is cut in a position within the guide 1 so that upon insertion of the guide 1 into the prosthesic cavity, formed after the removal of the prosthesis being discarded, it aligns with the predetermined plane. A short suitably shaped surgical grade reciprocating saw blade head, with a suitable follower adapted to align the saw head with the groove 3 and to follow the profile of the base of the groove 3, can be introduced into the groove 3 and gradually advanced therealong while being actuated by a suitable reciprocating device.

In some circumstances the saw head can be initially inserted, followed by the guide 1 and the cutting action advanced from the cavity interior towards the exterior.

Figure 5:
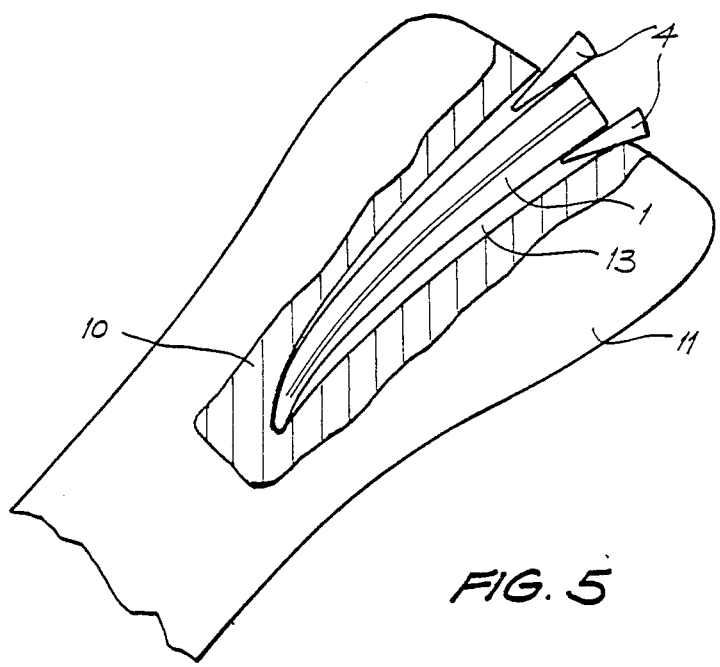

It is possible to use, in a similar fashion to that described above, a guide 1 which is a close fit but somewhat smaller that the stem of the discarded prosthesis. Such a guide 1 is shown in FIG. 5 in place in a bone and secured by a wedge 4. One advantage of this embodiment is that the exact size of the stem of the prosthesis to be discarded does not have to be known before commencing the removal operation.

In FIG. 6 the guide 1 is seen to have a fluid tight bladder 5 which is attached on the side opposite the groove 3. The guide 1 can be placed in the cavity of the cement to be removed before fluidly pressurising the bladder 5. The pressurized bladder 5 then rigidly fixes the guide 1 within the cavity.

Clearly in the above described guides the template is an integral part of the guide being the profile of the base line of the guide groove 3. However, the template may be quite separate from the guide.

An embodiment having separate guide and template is shown in FIG. 7. A template 6 is produced by a similar method as used in producing the guide 3 of the previous embodiments, using the equipment described with relation to FIG. 3. The template 6 is rigidly attached to a base 7 which is secured by suitable means to the end of the bone 11 containing the cement 10 to be removed. The saw includes a saw head 8 on the end of a wand 9 which is attached to a suitable reciprocating device. A portion of the wand 9 includes a template follower 15. The wand 9 is guided by a guide device 14 which may be spring biased or the wand 9 itself may be resiliently flexible. In this embodiment the profile of the template 6 may be approximately a mirror image of the cement/bone interface profile at the line being cut depending upon the relative positions of the device 14 and the follower 15.

A further embodiment with an external template separate to the guide is shown in FIG. 8. A lever 26 is pivotally attached to the end of a rigid arm 27. The arm 27 is advanced through stationary guides 14. The template follower 15 is also pivotally attached to the arm 27, the template follower 15 and lever 26 being coupled by tie rod 16. The template follower 15 is biased by a tensioned spring 17. The template 6 is arranged relative to the guides 14 such that the template follower 15 advances with the arm 27 along the template, the angle between the follower 15 and the arm 27 altering in response to the profile of the template 6. Such alteration of angle of the template follower 15 is reflected in an angular movement of the lever 26 causing movement transverse of the arm 27 corresponding to profile changes in the template 6 so that it follows the desired cement/bone interface. The saw head 8 is attached to an end of the wand 9 and maintained alongside the lever 26 so as to be biased by the lever 26 toward the cement during the cutting action obtained by reciprocative movement of the wand 9. The cut will progress transversely into the cement until the follower 15 comes up against the template 6. The template 6 and guides 14 are rigidly held by a grooved guide similar to that shown in FIG. 4. In this case the base of the groove 3 is flat.

Figure 9:
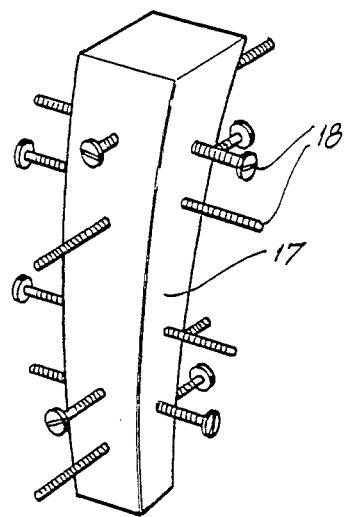
FIG. 9 schematically shows an alternative device, somewhat similar to the devices of FIGS. 4 and 5, which also embodies the invention.

FIG. 9 shows a guide holder 17 which is fixedly positioned approximately centrally of the cavity 13 by suitable adjustment of the various screws 18. Suitable guides having grooved templates similar to the grooves of the guides 1 of FIGS. 4 and 5 can be attached to the support 17 and used to produce a corresponding cut 12 in the cement 10. The support 17 could also be used to position devices such as those described in FIGS. 7 and 8.

Figure 10:
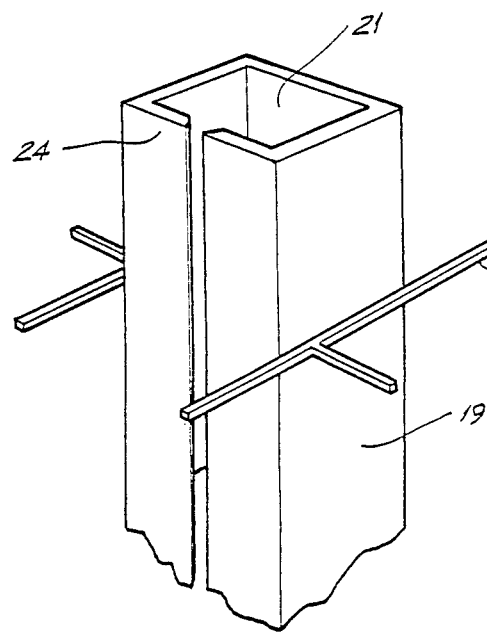
FIG. 10 schematically shows another alternative embodiment of the invention.

An alternative type of guide 19 is shown in FIG. 10. A system of spacers 20 are attached to the exterior of the guide 19 so as to hold it in a desired position within the cavity 13. The guide 19 includes a generally longitudinally running groove 21 with flanges 24 partially closing off the transverse entrance of the groove 21.

Figure 11:
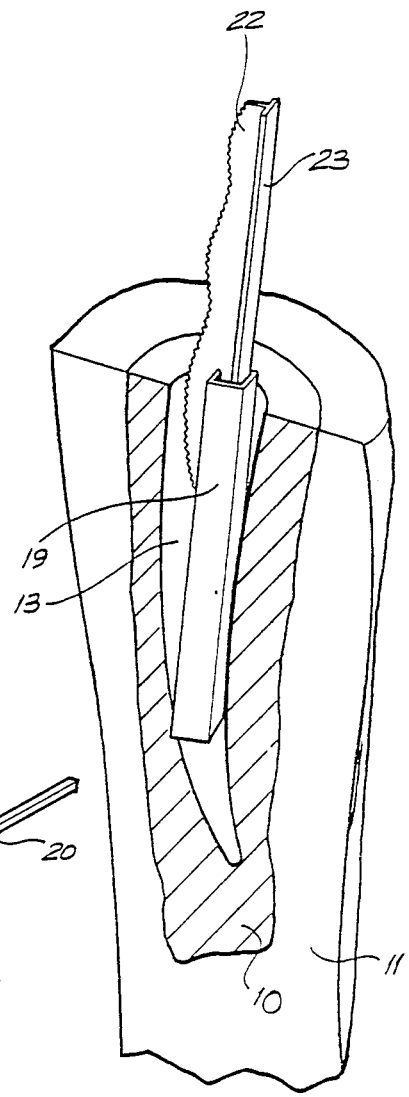
FIG. 11 shows schematically the device of FIG. 10 in cooperation with a blade in use in carrying out a method embodying the invention.

FIG. 11 shows the guide 19 of FIG. 10 situated within a cavity 13 (the bone 11 cement 10 combination being cross-sectioned in the Figure), in cooperation with a suitable saw 22. The cutting edge of the saw 22 is profiled in the manner of the templates 6 of the embodiment shown in FIGS. 7 and 8. The profiled saw is produced by a method similar to that described with reference to FIG. 3 above. The base 23 of the saw 22 is initially proximate the base of the groove 21 of the guide 19. After positioning the blade 22 longitudinally in the guide 19 it is reciprocated by a suitable device and advanced transversely of the guide 19 so as to simultaneously cut along the entire length of the desired cut 12. When the base 23 of the saw 22 reaches the flanges 24 it is prevented from further transverse movement. The dimensions of the groove 21 and saw 22 are pre-selected so that at this position the saw has completed the cut and cut 12 has progressed completely through the cement 10 but not substantially into the bone 11.

I claim:

1. A template having a profile corresponding to a profile of a line of intersection of a generally longitudinal pre-selected plane of a joint prosthetic cavity and an associated prosthetic cement/bone interface of a patient, the template comprising a guide shaped as a stem of a prosthesis to be replaced in the patient, and including a longitudinally running groove positioned in a plane of the guide corresponding in orientation to the pre-selected plane and including a groove base with a profile within said plane being the template profile.

2. A method of forming a guide means for use in removing prosthetic cement from a bone of a patient at a prosthetic cement/bone interface comprising the steps of determining a profile of the prosthetic cement/bone interface along a predetermined line running longitudinally of the bone and forming said profile on said guide means for guiding a suitable cutting means such that it may cut through the cement along said line substantially without cutting into the bone.

3. A product produced by carrying out the method of claim 2.

4. Apparatus comprising:
a template having a profile corresponding to a profile of a line of intersection of a generally longitudinal pre-selected plane of a joint prosthetic cavity and an associated prosthetic cement/bone interface of a patient;
a linear saw guide being rigidly attached to, or integral with, the template;
a saw adapted for reciprocating cutting action and traversable along the guide for linear advancement of the cutting action; and
a template follower connected with the saw for urging the saw to cut along a path being substantially the line of intersection of the pre-selected plane and the cement/bone interface.

5. Apparatus as defined in claim 4 wherein the guide is shaped as a stem of a prosthesis to be replaced in the patient, and including a longitudinally running groove positioned in a plane of the guide corresponding in orientation to the pre-selected plane and including a groove base with a profile within said plane being the template profile and the apparatus further comprises wedges adapted to firmly secure by wedging action the guide within a prosthetic cavity around which the cement is to be removed.

6. Apparatus as defined in claim 4 further comprising a base on the template and adapted so that the base is firmly attachable to a bone end in which prosthetic cement is to be removed and with the template and bone on opposite sides thereof, the base including an aperture for insertion of said saw, and wherein said saw being a saw head at one end of a wand and the opposite end of the wand including an attachment for connection to a reciprocating device and said saw guide is rigidly attachable to the base and positioned and shaped so as to guide said saw wand through said aperture during longitudinal advancement of the saw.

7. Apparatus as defined in claim 6 wherein said wand is elastically transversely flexible.

8. A method of producing a template including the steps of:
scanning a patient in an area of a joint prosthesis so as to obtain a profile of a prosthetic cement/bone interface at its intersection with a longitudinal pre-selected plane through a medullary cavity in the bone; and
feeding the profile into a machine which, in response thereto, forms the template with a surface having said profile.

9. A method of removing prosthetic cement from a bone of a patient comprising producing a template by scanning a patient in an area of a joint prosthesis so as to obtain a profile of a prosthetic cement/bone interface at its intersection with a longitudinal pre-selected plane through a medullary cavity in the bone; feeding the profile into a machine which, in response thereto, forms the template with a surface having said profile, removing the prosthesis to be discarded leaving a prosthetic cavity, cutting at least one longitudinally running cut in the prosthetic cement without substantially cutting the bone by using said surface as a cutting guide so as to form a number of arcuate prosthetic cement parts and removing each cement part.

10. A method for removing prosthetic cement from a bone of a patient undergoing a joint prosthesis replacement operation, comprising the steps of:
(a) producing a template profiled so as to correspond to the profile of the line of intersection of a generally longitudinally pre-selected plane of a joint prosthesis cavity and an associated cement/bone interface of the patient by,
(i) scanning the patient in the area of the joint prosthesis so as to obtain a profile of the said prosthetic cement/bone interface at its intersection with the said pre-selected plane, and
(ii) forming on a template blank a template surface having a profile corresponding to the profile of the said line of intersection,
(b) removing the prosthesis to be replaced from the prosthetic cavity,
(c) positioning the template in relation to the prosthetic cavity for guiding a cutting blade along the template to form a running cut substantially completely through the prosthetic cement along the said line of intersection and substantially without cutting the adjacent bone and guiding the blade along the template to form said cut,
(d) replacing at least once the steps (a) and (c) along the line of intersection of one or more other generally longitudinal pre-selected planes of the joint prosthesis cavity and the associated cement/bone interface of the patient to form a number of segmented prosthetic cement pieces, and
(e) removing the segmented prosthetic pieces from the bone.

11. A method as claimed in claim 10 in which the scanning of the patient is carried out in an X-ray machine.

12. A method as claimed in claim 10 in which a bottom plug of the prosthetic cement is bared out before the running cuts are formed in the prosthetic cement.

13. A method as claimed in claim 10 in which at least three running cuts are formed in the prosthetic cement and the cuts are substantially equiangularly spaced around the prosthetic cavity.

* * * * *